US00PP26461P2

(12) United States Plant Patent
Kuang-Liang

(10) Patent No.: US PP26,461 P2
(45) Date of Patent: Mar. 8, 2016

(54) *POLIANTHES* PLANT NAMED 'CNGH'

(50) Latin Name: *Polianthes hybrida*
Varietal Denomination: CNGH

(71) Applicant: Huang Kuang-Liang, Chiayi (TW)

(72) Inventor: Huang Kuang-Liang, Chiayi (TW)

(73) Assignee: Berbee Beheer B.V., Lisse (NL)

( * ) Notice: Subject to any disclaimer, the term of this patent is extended or adjusted under 35 U.S.C. 154(b) by 178 days.

(21) Appl. No.: 13/999,245

(22) Filed: Jan. 31, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — C. A. Whealy

(57) ABSTRACT

A new and distinct cultivar of *Polianthes* plant named 'CNGH', characterized by its upright plant habit; numerous bright yellow-colored flowers; flowers arranged on upright and strong flower scapes; pleasant fragrance; and good garden performance.

2 Drawing Sheets

Botanical designation: *Polianthes hybrida.*
Cultivar denomination: 'CNGH'.

BACKGROUND OF THE INVENTION

The present invention relates to a new and distinct cultivar of *Polianthes* plant, botanically known as *Polianthes hybrida* and hereinafter referred to by the name 'CNGH'.

The new *Polianthes* plant originated from an open-pollination in 2001 in Chiayl City, Taiwan of a proprietary selection of *Polianthes tuberosa*×*Polianthes howardii* identified as code number 84-E-14, not patented, as the female, or seed, parent with an unknown selection of *Polianthes hybrida* as the male, or pollen, parent. The new *Polianthes* plant was discovered and selected by the Inventor as a single flowering plant within the progeny of the stated open-pollination in a controlled greenhouse environment in Chiayl City, Taiwan in April, 2002.

Asexual reproduction of the new *Polianthes* plant by divisions in a controlled environment in Puli, Taiwan since 2010 has shown that the unique features of this new *Polianthes* plant are stable and reproduced true to type in successive generations.

SUMMARY OF THE INVENTION

Plants of the new *Polianthes* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'CNGH'. These characteristics in combination distinguish 'CNGH' as a new and distinct *Polianthes* plant:

1. Upright plant habit.
2. Numerous bright yellow-colored flowers.
3. Flowers arranged on upright and strong flower scapes.
4. Pleasant fragrance.
5. Good garden performance.

Plants of the new *Polianthes* differ primarily from plants of the female parent selection in flower color as plants of the female parent selection have light lilac-colored flowers.

Plants of the new *Polianthes* can be compared to plants of *Polianthes tuberosa* 'The Pearl', not patented. In side-by-side comparisons, plants of the new *Polianthes* and 'The Pearl' differed in the following characteristics:

1. Plants of the new *Polianthes* were taller than plants of 'The Pearl'.
2. Leaves of plants of the new *Polianthes* were longer than leaves of 'The Pearl'.
3. Plants of the new *Polianthes* had shorter inflorescences with fewer flowers per inflorescence than plants of 'The Pearl'.
4. Plants of the new *Polianthes* and 'The Pearl' differed in flower color as plants of 'The Pearl' had white-colored flowers.

BRIEF DESCRIPTION OF THE PHOTOGRAPHS

The accompanying colored photographs illustrate the overall appearance of the new *Polianthes* plant showing the colors as true as it is reasonably possible to obtain in colored reproductions of this type. Colors in the photographs may differ slightly from the color values cited in the detailed botanical description which accurately describe the colors of the new *Polianthes* plant.

The photograph on the first sheet comprises a side perspective view of a typical flowering plant of 'CNGH' grown in a container.

The photograph on the second sheet is a close-up view of a typical inflorescence of 'CNGH'.

DETAILED BOTANICAL DESCRIPTION

The aforementioned photographs and following observations, measurements and values describe plants grown during the late summer in ground beds and containers in a glass-covered greenhouse in Lisse, The Netherlands and under cultural practices typical of commercial *Polianthes* production. During the production of the plants, day temperatures ranged from 12° C. to 32° C. and night temperatures ranged from 3° C. to 18° C. Plants were one year old when the photographs and description were taken. In the following description, color references are made to The Royal Horticultural Society Colour Chart, 2007 Edition, except where general terms of ordinary dictionary significance are used.

Botanical classification: *Polianthes hybrida* 'CNGH'.

Parentage:

*Female, or seed, parent*.—Proprietary selection of *Polianthes tuberosa*×*Polianthes howardii* identified as code number 84-E-14, not patented.

*Male, or pollen, parent*.—Unknown selection of *Polianthes hybrida*, not patented.

Propagation:

*Type*.—By tissue culture.

*Time to initiate roots, summer*.—About 20 days at soil temperatures about 20° C.

*Time to produce a rooted plant, summer*.—About 25 days at soil temperatures about 20° C.

*Root description*.—Medium in thickness, fleshy; grey in color.

*Rooting habit*.—Moderate branching; medium density.

*Rhizomes*.—Length: About 5 cm. Diameter: About 3 cm. Shape: Ovate. Texture: Smooth, glabrous. Color: Close to 155B and 158C to 158D.

Plant description:

*Plant form and growth habit*.—Herbaceous flowering perennial plant; upright plant habit with strong upright flower scapes; leaves and flowering stems basal; moderately vigorous growth habit.

*Plant height*.—About 74.5 cm.

*Plant width* (*spread*).—About 82 cm.

Leaf description:

*Arrangement and appearance*.—Leaves arranged in a basal rosette and along flower scape; leaves simple and sessile.

*Leaf length, rosette leaves*.—About 44.5 cm.

*Leaf width, rosette leaves*.—About 1.5 cm.

*Leaf length, flower scape leaves*.—About 13 cm.

*Leaf width, flower scape leaves*.—About 1.3 cm.

*Shape*.—Ligulate.

*Apex*.—Long acuminate.

*Base*.—Cuneate, decurrent.

*Margin*.—Entire.

*Texture, upper and lower surfaces*.—Smooth, glabrous.

*Venation pattern*.—Parallel.

*Color*.—Developing leaves, upper surface: Between 143A and 144A. Developing leaves, lower surface: Close to 137B. Fully expanded leaves, upper surface: Darker than between 143A and 146A; venation, darker than between 143A and 146A. Fully expanded leaves, lower surface: Close to N137A; towards the base, slightly dotted with close to 183C; main vein, close to 144A; secondary veins, close to N137A.

Flower description:

*Flower type and flowering habit*.—Trumpet-shaped flowers arranged in terminal racemes supported by strong upright scapes; flowers face mostly outwardly; freely flowering habit with about 26 flowers developing per inflorescence.

*Fragrance*.—Moderate; pleasant and sweet.

*Natural flowering season*.—Plants begin flowering about four months after planting; flowering continuous from early August into September in The Netherlands.

*Postproduction longevity*.—Flowers last about one week the plant; flowers not persistent.

*Flower buds*.—Height: About 4 cm. Diameter: About 6 mm. Shape: Narrowly oblanceolate. Color: Close to 2C.

*Inflorescence height*.—About 15.3 cm.

*Inflorescence diameter*.—About 11 cm.

*Flower diameter*.—About 1.8 cm.

*Flower depth*.—About 5 cm.

*Perianth*.—Quantity and arrangement: Typically six segments arranged in two whorls; lower 20% of the segments are fused into a narrow tube; upper free part of segments flaring outwardly. Segment length: About 5.2 cm. Segment width: About 7 mm. Segment lobe shape: Oblanceolate. Segment apex: Short apiculate. Segment margin: Entire. Segment texture, upper and lower surfaces: Smooth, glabrous; moderately velvety. Segment color: When opening, upper surface: Close to 10B; tube, close to 8C. When opening, lower surface: Close to 10A; tube, close to 10B. Fully opened, upper surface: Close to 11B; tube, close to 11C; color becoming closer to 11A and apices closer to 16B with development. Fully opened, lower surface: Close to 10A; tube, close to 10B.

*Peduncles* (*flower scapes*).—Length: About 69.1 cm. Diameter: About 5 mm. Aspect: Upright. Strength: Strong. Texture: Smooth, glabrous. Color: Close to between 143B and 144A covered with thin waxy layer, close to 138B.

*Pedicels*.—Length: About 1 mm. Diameter: About 1.75 mm. Aspect: About 40° from peduncle axis. Strength: Strong. Texture: Smooth, glabrous. Color: Close to 145A to 145B.

*Flower bracts*.—Arrangement: One at the base of the pedicel. Length: About 1.6 cm. Width: About 4 mm. Shape: Narrowly deltoid. Apex: Narrowly acute. Base: Cuneate. Margin: Entire. Texture, upper and lower surfaces: Smooth, glabrous. Color, upper and lower surfaces: Close to 145A; towards the base, close to 145D.

*Reproductive organs*.—Stamens: Quantity per flower: Typically six. Filament length: About 7 mm. Filament color: Close to 11C. Anther shape: Narrowly oblong; dorsifixed. Anther length: About 0.8 mm. Anther color: Close to 150B to 150C. Pollen amount: Moderate. Pollen color: Close to 4A. Pistils: Quantity per flower: One. Pistil length: About 1.9 cm. Style length: About 1.85 cm. Style color: Close to 154C to 154D. Stigma shape: Clavate. Stigma color: Close to 150B. Ovary color: Close to 145B.

*Seeds and fruits*.—Seed and fruit development have not been observed on plants of the new *Polianthes*.

Disease & pest resistance: Plants of the new *Polianthes* have not been noted to be resistant to pathogens and pests common to *Polianthes* plants.

Garden performance: Plants of the new *Polianthes* have been observed to have good garden performance and to tolerate rain, wind, high temperatures about 32° C. and to be hardy to USDA Hardiness Zone 8b.

It is claimed:

1. A new and distinct *Polianthes* plant named 'CNGH' as illustrated and described.

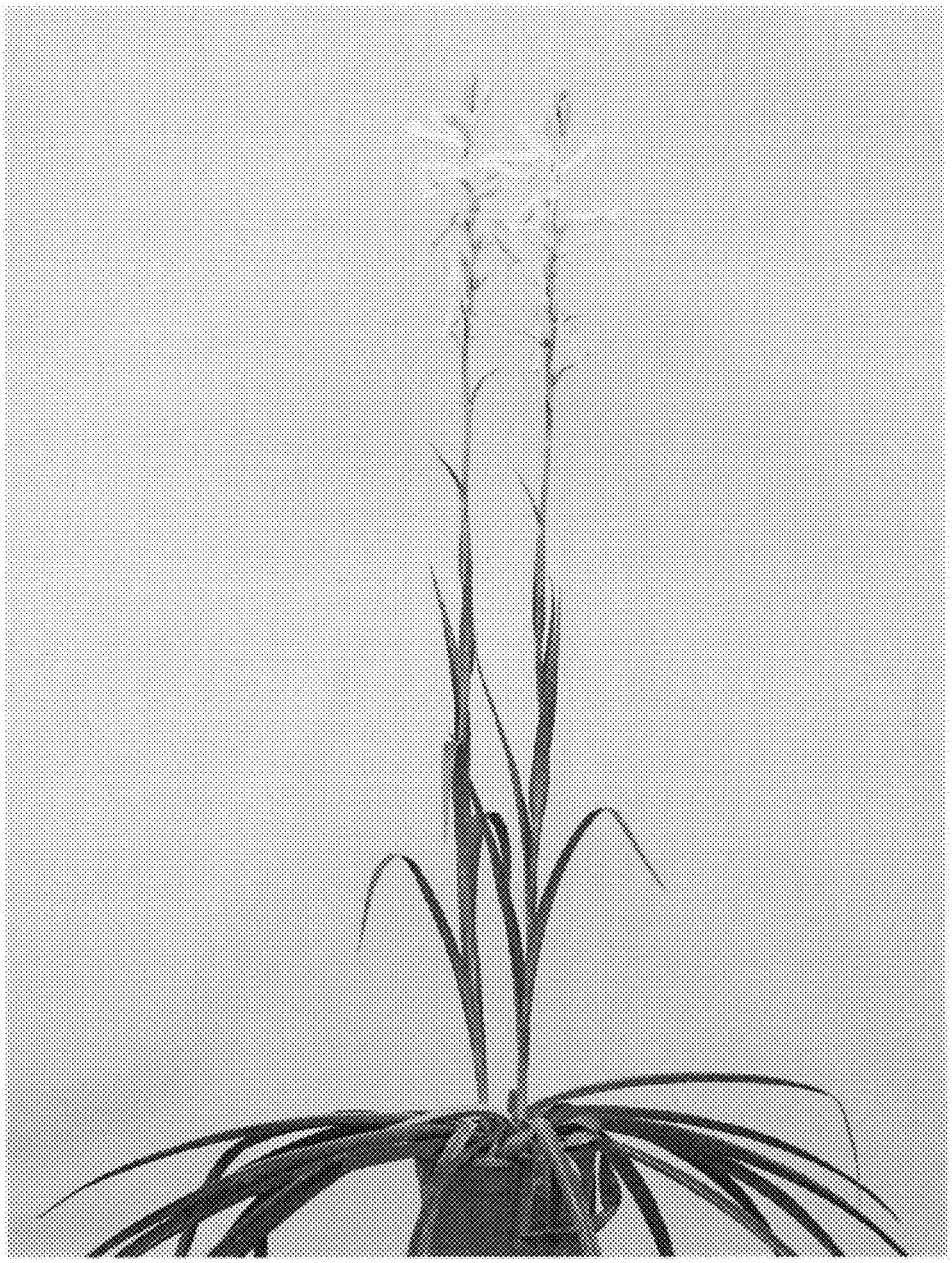

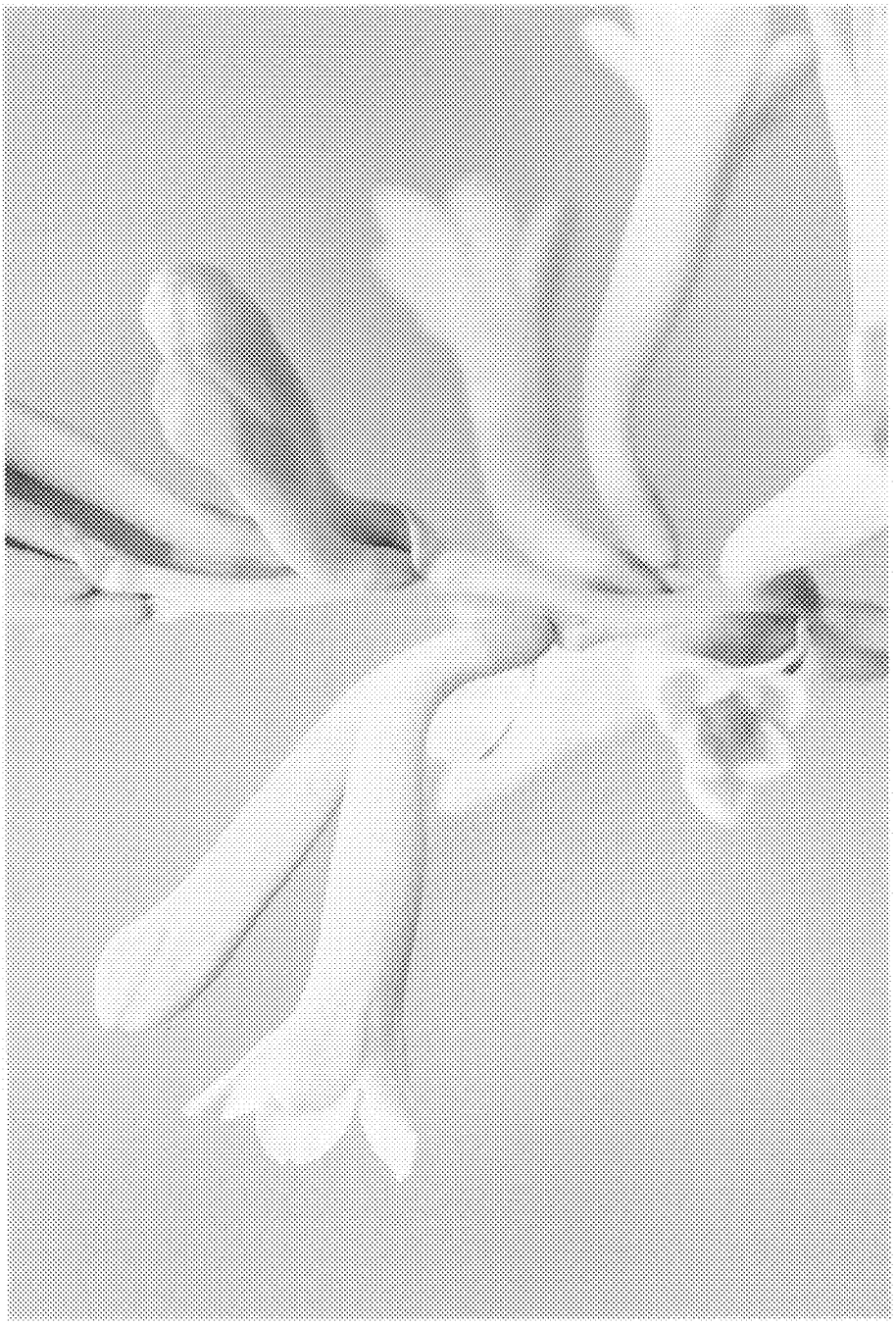

* * * * *